United States Patent [19]

Gordon

[11] Patent Number: 4,943,524
[45] Date of Patent: Jul. 24, 1990

[54] ENZYME IMMUNOASSAY FOR CANCER PROCOAGULANT

[75] Inventor: Stuart G. Gordon, Denver, Colo.

[73] Assignee: The University of Colorado Foundation, Inc., Boulder, Colo.

[21] Appl. No.: 313,285

[22] Filed: Feb. 17, 1989

Related U.S. Application Data

[63] Continuation of Ser. No. 69,454, Jul. 2, 1987, abandoned, which is a continuation of Ser. No. 606,330, May 2, 1984, abandoned, which is a continuation-in-part of Ser. No. 391,278, Jun. 23, 1982, Pat. No. 4,461,833.

[51] Int. Cl.$^5$ ................. G01N 33/53; G01N 33/531; G01N 5/00; C12P 21/00
[52] U.S. Cl. ....................................... 435/7; 436/543; 436/547; 436/813; 436/548; 530/387; 435/240.27; 435/172.2; 435/70.21
[58] Field of Search ............... 435/7, 240.27, 172.2, 435/68; 530/387; 436/543, 547, 548, 813

[56] References Cited

U.S. PATENT DOCUMENTS 4,368,262 1/1983 Bucovaz ........................... 435/13 X
4,461,830 7/1984 Philpot ................................ 435/13
4,628,027 12/1986 Gay ....................................... 435/7

OTHER PUBLICATIONS

Chemical Abstracts, 95:166538t (1981).
Gordon, S. G., J. Histochem. Cytochem., 29(3A), 457–463 (1981).
Kohler, G., et al., Nature, 256 (5517), 495–497 (Aug. 7, 1975).
Gordon et al. (1975), Thromb. Res. 6:127–138.
Gordon et al. (1978), Cancer Res. 38:2467–2472.
Gordon et al. (1976), J. Natl. Cancer Inst. 62:773–776.
Gordon et al. (1979), Proc. Am. Assoc. Cancer Res. 20:177.
Gordon et al. (1979), Clin. Res. 27:54.
Gordon et al. (1981), J. Clin. Invest. 67:1665–1671.
Gordon et al. (1981), J. Histochem. Cytochem. 29:457–463.
Gordon et al. (1981), Clin. Res. 29:65A.
Gordon et al. (1982) Thromb. Res. 26:379–387.
Gordon et al. (1984), Proc. Ann. Meet. Am. Soc. Clin. Oncol., 3:6.
Gordon et al. (1984), Clin. Res. 32:415.

*Primary Examiner*—Christine M. Nucker
*Assistant Examiner*—Karne J. Krupen
*Attorney, Agent, or Firm*—Greenlee and Associates

[57] ABSTRACT

A procedure for the immunoassay of a proteolytic procoagulant enzyme in biological samples is described. The presence of the enzyme is indicative of malignant disease, and the immunoassay is used as a diagnostic test for cancer.

9 Claims, No Drawings

ENZYME IMMUNOASSAY FOR CANCER PROCOAGULANT

Partial funding for research disclosed in this instrument was received from the United States Government. The government, as a result of such partial funding may have an interest in the disclosed technology.

This application is a continuation of application Ser. No. 069,454, filed July 2, 1987, now abandoned, which is a continuation of United States Patent Application 606,330, filed on May 2, 1984, now abandoned, which in turn is a continuation in part application of United States Patent Application 391,278, filed on June 23, 1982, and now U.S. Pat. No. 4,461,833.

The present invention describes a procedure for a highly sensitive and specific immunoassay of a proteolytic procoagulant enzyme in biological samples, for example biological fluids such as human and animal serum, plasma, tissue extracts and histologic sections. The presence of this enzyme is indicative of malignant disease, and the immunoassay described is used as a diagnostic test for cancer.

For years, investigators have sought to identify substances that are unique to tumor cells for use as diagnostic markers of cancer. In 1970, Bubenek et al, reporting in *Int. J. Cancer* 5:310 (1970), demonstrated that serum from cancer patients contained antibodies that bound to tumor cell surface antigens. Subsequently, many antigens were reported found on the surface of human melanoma and on other neoplastic cells. Some of these antigens have been identified with normal fetal tissue, for example antigens common to human colonic carcinomas and fetal gut epithelium. Since fetal tissue is comprised of undifferentiated cells, and neoplastic cells are "dedifferentiated cells", the accepted working hypothesis for tumor antigens or oncofetal antigens is that certain proteins are expressed by cells in their undifferentiated state, and the expression of these proteins is suppressed when undifferentiated cells become differentiated into normal cells. If these normal cells become dedifferentiated during the malignant transformation process, the genetic information is derepressed and these tumor antigens are again expressed. An alternative school of thought suggests that partially differentiated "stem" cells of normal adult tissues are held in their partially differentiated state by carcinogenic agents, and these partially differentiated cells are able to multiply in an uncontrolled fashion. In either case, malignant transformation is recognized to result in the genetic expression of protein antigens that are associated with the undifferentiated cell.

Many tumor antigens have been identified and characterized during the past 20 years. Most notable among these are carcinoembryonic antigen (CEA), alpha-fetoprotein (AFP) and acute lymphoblastic leukemia associated antigen (cALLA). Carcinoembryonic antigen was first described by Gold and Friedman (*J. Exp. Med.* 121:439 (1965)) who detected it in colon carcinomas and fetal gastrointestinal tract tissue. CEA is a high molecular weight (180–200 kd) protein that is composed of 45–57% carbohydrate and 30–46% protein. CEA, or CEA-like material, is produced by a variety of mucin producing normal epithelial tissues including normal colon. In addition, a variety of nonmalignant disorders are associated with elevated plasma levels of CEA including peptic ulcers (10%), pancreatitis (27%), inflammatory bowel diseases (15–40%), hepatic disease, including hepatitis, jaundice, biliary tract disease and cirrhosis (20–80%). In addition, CEA levels have been widely studied as predictive of various types of malignant disease including tumors of the GI tract (30%), gastric cancer (72%), pancreatic cancer (88%), breast cancer (24%), lung and respiratory tract tumors (30%) and gynecological tumors (10%) (J. D. Beatty, et al, *Prog. Clin. Cancer* 8:9 (1982)). There appears, however, to be no close correlation between the type and size of the tumor and the plasma CEA level; although patients with metastatic disease and stage 4 cancer appear to have higher levels than patients without metastatic disease or early stage malignancy. CEA levels have been helpful in followup studies of breast and colorectal cancer; if the tumor is CEA-positive, monitoring CEA levels has been found to provide important information as to the efficacy of therapeutic treatment of the disease.

Alpha-fetoprotein is a protein of about 70 kd with amino acid composition similar to that of serum albumin (11,12), is produced by fetal liver and can be detected in amniotic fluid and maternal serum. Alpha-feto protein has also been found to be present in hepatocellular carcinoma. AFP is elevated in the serum of about 80% of patients with liver tumors, almost all those with teratocarcinomas, 15% of patients with gastric carcinoma, 3% of patients with colorectal carcinoma, 24% of patients with hepatic carcinoma, and 25% of patients with biliary tract carcinomas (see Ruddon, *Semin. Oncol.* 9:416 (1982) and McIntire, et al, *Cancer Res.* 35:991 (1975)). AFP rises as a function of a variety of insults to the liver and in pregnancy. In spite of the apparent high predictive value of AFP for cancer and a small number of non-cancer diseases that appear to have elevated AFP levels, the overall value of AFP as a tumor marker is low.

Recently, acute lymphoblastic leukemia antigen (cALLA) has been studied to determine its effectiveness in identifying acute lymphoblastic leukemia patients (see Ritz, et al, *Nature* 283:583 (1980)). Although initial studies suggested that cALLA was specific for acute leukemic cells, more recently the antigen has been found on a variety of normal cell types including normal kidney epithelium and melanomas. Its efficacy as a diagnostic marker of leukemia is yet to be firmly established.

There are a large number of other tumor associated antigens that have been studied for their potential as tumor markers. Tumor markers to the following human cancers are reviewed by Hellstrom et al, *Springer Semin Immunopathol* 5:127 (1982): melanoma, neuroblastoma, glioma, colorectal carcinoma, gastric carcinoma, mammary carcinoma, brachiogenic carcinoma, pancreatic carcinoma, ovarian carcinoma, Wilms' tumor, renal cell carcinoma, transitional cell carcinoma of the bladder, osteogenic sarcoma, carcinoma of the uterine cervix and lymphoma. These tumor antigens are poorly characterized and have not been carefully tested for their ability to diagnose clinical cancer. None of them have proven value as tumor markers or as diagnostic indicators of cancer.

Cancer procoagulant was originally identified during my studies to seek a substance that initiated the abnormal blood coagulation associated with malignant disease. This protein has been purified to homogeneity and characterized. It is a cysteine protease that initiates coagulation by directly activating factor X in the coagulation cascade.

Cancer procoagulant appears to have no carbohydrate (<1 mole sialic acid, or hexose/mole of cancer procoagulant), it has a molecular weight of 68,000 from all species that have been examined, including mouse, rabbit, and human. Cancer procoagulant is eluted from a 1.5 M agarose gel filtration column in the void volume indicating that the protein aggregates into a very high molecular weight complex ($1.5 \times 10^6$ daltons) during this type of gel filtration procedure. It is a single polypeptide protein with the molecular weight of 68 kd and an isoelectric point of 4.8. It is inhibited by mercury and iodoacetamide, properties that are characteristic of cysteine proteases. To determine the distribution of cancer procoagulant activity in various tumor types, a variety of human tumor extracts and some of their normal tissue counterparts and a variety of serumfree culture media from transformed cells and media from their normal cell counterparts were examined. It was found that cancer procoagulant activity existed in extracts of malignant cells and tissue culture medium from transformed cells, but not in extracts of normal tissue and serum-free medium from normal cells and culture.

It is the objective of the present invention to develop antibodies to cancer procoagulant antigen.

A second objective of the present invention is to use antibodies to cancer procoagulant antigen to develop an immunoassay for this antigen in biological samples, including serum, plasma, tissue extracts, urine and histologic sections.

The final object of the present invention is to develop an antibody and an immunoassay for cancer procoagulant antigen in order to quantitate the level of this antigen with high sensitivity, specificity and accuracy in biological samples.

The following description is presented in order to provide a thorough understanding of the subject matter in the experimental procedures used in the present application. It is intended to illustrate an embodiment of the present invention, and is not to be construed as limiting the scope of the present invention.

EXAMPLE I

Cancer Procoagulant Antigen

Purified cancer procoagulant antigen was obtained from rabbit V2 carcinoma, human amnion-chorion tissue or other cellular sources, according to procedures described in U.S. Pat. No. 4,461,833. Briefly, tissue, e.g., surgically removed rabbit V2 carcinoma, was extracted in 3 changes of veronal buffer, the extracts were pooled and concentrated 10-fold and used as a source of cancer procoagulant antigen. The original purification technique followed the 4 step chromatographic procedure described in the Patent Application. It involved benzamidine-Sepharose affinity chromatography, 1.5 M agarose gel filtration column chromatography, a second benzamidine-Sepharose affinity chromatography column and a phenyl-Sepharose hydrophobic affinity chromatography column step. The protein purified by this method had all of the proper enzymatic and chemical characteristics of cancer procoagulant and was used as an antigen to immunize a goat by standard techniques described in Example II. The partially purified goat antibody preparation was coupled to cyanogen bromide activated Sepharose and a $1.5 \times 20$ cm immunoaffinity chromatography column was prepared In the second purification technique, the extract sample was applied to the immunoaffinity resin in 20 mM veronal buffer, the column was placed on a rotating wheel and allowed to rotate overnight so that the sample and resin were thoroughly mixed. The next morning the column was allowed to settle and the column was washed with 20 mM veronal buffer until all unbound protein was washed off the column (the absorption at 280 nm is the same as that of the buffer); this required from 250-350 ml of buffer. The column was washed with 100 ml of 5% deoxycholate dissolved in 20 mM veronal buffer [deoxycholate should be recrystallized from acetone:water (3:1)] followed by 3-4 column volumes of 20 mM veronal buffer. This removed all adsorbed proteins from the column. The column was eluted with 100 ml of 3 M NaSCN followed by 50-100 ml of veronal buffer. The eluate was dialyzed immediately against 20 mM BisTris propane buffer (pH 6.5) at 5° overnight. The dialyzed eluate was concentrated on an Amicon PM10 ultrafiltration membrane and assayed for activity as described below. Every third or fourth run the column was cleaned with 5 M NaSCN and reequilibrated with veronal buffer. This immunoaffinity procedure removed the majority of contaminating proteins from the cancer procoagulant sample.

A p-chloromercurial benzoate (PCMB) organomercurial Agarose column (Affi-gel 501) was purchased from Bio-Rad. The column was prepared according to the Bio-Rad technical information. The column was equilibrated in 20 mM Bis-Tris propane buffer (pH 6.5). The sample was applied to the column and washed slowly onto the column with 20 mM Bis-Tris propane buffer. The column was allowed to stand for 1 hr at 4° C. and washed slowly overnight with 20 mM Bis-Tris propane buffer. When the absorption at 280 nm was the same as that of the Bis-Tris propane buffer, the column was washed with about 50 ml of 1 M urea and 1% Tween in water and followed by enough 20 mM Bis-Tris propane buffer to completely remove all residual Tween-urea from the column The column was eluted with $HgCl_2$ or glutathione, and each elution was dialyzed immediately in 20 mM Bis-Tris propane buffer at 4° C. overnight with several changes of buffer. The samples were concentrated on a PM10 ultrafiltration membrane and checked for activity as described above. The purified samples from the goat immunoaffinity column and the PCMB affinity column were evaluated by SDS-polyacrylamide gel electrophoresis and the protein content of each sample was determined with the Lowry protein determination. The activity in the samples was preserved by making them 1 mM with $HgCl_2$ which will inhibit and preserve the activity for later use.

EXAMPLE II

Anti-Cancer Procoagulant Goat IgG

One hundred micrograms of purified CP was emulsified in an equal volume of complete Freund's adjuvant and injected subcutaneously in multiple sites along the goat's spine. Booster immunizations were made at 3 week intervals by suspending 30-50 µg of purified CP in equal volume of incomplete Freund's adjuvant and injecting the goat in the same way. Blood samples were obtained by jugular vein venipuncture at monthly intervals and tested for antibody by crossed immunodiffusion. After 4 months, an antibody titer of 1:16 was reached. This level of antibody has been sustained for a minimum of 12 months. The goat antibody (a polyclonal IgG immunoglobulin) was partially purified from goat serum by ammonium sulfate precipitation and DEAE-cellulose ion exchange chromatography by standard techniques. The partially purified antibody was found to contain antibodies to rabbit serum proteins, probably minor contaminants from the purified CP preparations of rabbit V2 carcinoma. To remove these contaminating antibodies, rabbit serum was coupled to cyanogen bromide activated Sepharose to form a normal rabbit serum protein affinity column, and the partially purified goat antibody preparation was passed over the normal rabbit serum column to remove the contaminating antibodies. The resulting goat IgG preparation was free of cross reacting antibodies with normal rabbit serum. These partially purified goat antibodies were used for immunoaffinity chromatography and in the immunoassay system.

EXAMPLE III

Monoclonal Antibodies

Using the second purification technique described above, mice were immunized with purified CP to raise B cell antibodies as described by Yelton et al, in *Monoclonal Antibodies* (Kennett et al, editors) Plenum Press (N.Y.), 1980, pgs. 3–17, although other means of raising hybridoma antibodies may also be employed. Briefly, 40 $\mu$g of purified antigen were suspended in an equal volume of complete Freund's adjuvant and injected subcutaneously into Balb/C mice. This was followed by 2 injections of 35 and 10 $\mu$g amounts of antigen suspended in incomplete Freund's adjuvant and injected subcutaneously at monthly intervals. Three weeks after the last subcutaneous immunization, 3 intraperitoneal immunizations of 10 $\mu$g, 70 $\mu$g and 70 $\mu$g of antigen in saline were administered intraperitoneally at 3 day intervals, 2 weeks later a blood sample was obtained by retroorbital bleeding and tested for serum antibody by crossed immunodiffusion; having confirmed the presence of an antibody, a last intraperitoneal immunization (40 $\mu$g) was administered, and 3 days later the animals were sacrificed. The spleen lymphocytes were removed and hybridized with P3/X 63AG8.653 variant of the mouse myeloma cell line with 50% polyethylene glycol (17,18). Hybrid cells were plated in a 96 well microtiter plate with $2 \times 10^6$ normal murine spleen cells as a feeder layer, and unhybridized myeloma cells were eliminated by growing the cultures in HAT medium for 4 weeks. An ELISA was used to screen the medium from the microtiter wells for antibody producing cells. In this assay purified antigen was adsorbed to the surface of the microtiter wells, the wells were blocked with 2% BSA, and media was incubated in the wells for 1 hr at 37° C., and an alkaline phosphatase labeled rabbit antimouse immunoglobulin preparation was added to identify the antibodies that had attached to the antigen. Positive wells were expanded in the presence of $2 \times 10^6$ normal spleen cells. Expanded wells were retested and positive wells were cloned 2 more times at low density to obtain clean and stable populations of hybrid cells for use in the experiments. Three clones were identified, each clone produced IgMk antibodies to cancer procoagulant antigen.

The IgM samples obtained from the hybrid cells (either as medium from tissue cultured cells or ascites fluid) contained procoagulant activity. In a representative experiment, Balb/C mice were injected with 0.5 ml of pristane to desensitize their immune system. Three weeks later, the mice received $2 \times 10^6$ hybridoma cells intraperitoneally, and ascites fluid was drained 3 or 4 times at 2 day intervals from the mice by intraperitoneal needle stick until the mice died. Ascites fluid was assayed for procoagulant activity, activity in factor VII-depleted plasma and inhibition by mercury and the procoagulant activity was tentatively characterized as that of cancer procoagulant. Since cancer procoagulant is believed to be an oncofetal antigen, and hybrid cells are developed from a malignant cell line (the myeloma variant), it is understandable how the antigen could be associated with the hybrid cells. Therefore, it is also probable that the IgM antibody is bound to the antigen in the ascites fluid, rendering it immunologically unreactive in the assay system. Therefore, it was necessary to separate the antigen from the antibody so that the antibody was rendered immunologically reactive to antigen in other samples. The ascites fluid was made 3 M with urea and applied to a $1 \times 90$ cm 1.5 M agarose gel filtration column that was preequilibrated in 3 M urea. The sample was eluted from the column in 3 M urea and the first peak (void volume) was assayed for IgM and procoagulant activity; it was free of procoagulant activity and contained all of the IgM. A second peak from the column contained procoagulant activity and no IgM. Fractions from the first peak were pooled, dialyzed against at least 3 changes of 5 mM Tris-HCl buffer (pH 7.5), the sample was concentrated over an Amicon XM50 ultrafiltration membrane, and refrigerated overnight in a centrifuge tube. The next morning, a precipitate had formed in the test tube, it was removed by centrifugation and resuspended in PBS. The resuspended precipitate sample was found to contain the immunoreactive IgM fraction, and a small amount had remained behind in the supernatant. This purified IgM was assayed against purified antigen, using 2% normal human serum as a control blank and gave a sample to blank ratio of from 10 to 20. The unpurified ascites gave a sample to background ratio of from 2 to 4, the supernatant gave a sample to background ratio of 6 to 10. This purified IgM was then used in the immunoassay. There are other methods for dissociating antigen-antibody complexes so they can be separated. Such methods may include higher concentrations of urea, low pH (pH 2–3.5), 5M guanidine-HCl, high pH (pH 10.5–12) and combinations of dissociating agents and pH adjustment. All such methods for separating antibody-cancer procoagulant antigen complexes are included within the perview of this application.

EXAMPLE IV

Immunoassay

Two separate immunoassays for the quantification of cancer procoagulant were developed.

The first immunoassay system was a direct ELISA in which antigen was adsorbed to the surface of the wells in a 96 well Immulon I microtiter plate at room temperature for 2 hrs, the well was rinsed with phosphate buffered Tween-20, the open sites on the wells were blocked with 2% normal human serum in phosphate buffer at 37° C. for 1 hr, and the wells were washed 3 times with 20 mM phosphate buffer (pH 7.5) containing 0.05% Tween-20. Purified IgM antibody was diluted 1:200 in phosphate buffer and 50 1 was added to each well and incubated at 37° C. for $\mu$1 hr. The wells were washed 3 times with phosphate buffer containing 0.05% Tween (PTB). One to 1000 dilution of alkaline phosphatase labeled rabbit antimouse IgM antibody was added to each well, incubated for 1 hr at 37° C., the wells were washed with PTB and 100 $\mu$1 of p-nitrophenyl phosphate (5 mg/ml) in 10% diethanolamine buffer (pH 9.8)

containing 0.1 mg MgCl$_2$.6H$_2$O/ml and 0.2% NaN$_3$ and incubated at 37° C. for from 45 to 90 min (until color intensity is adequate to read), and then the plate was read on a Dynatech microtiter plate reader which measured absorbance at 405 nm.

In a second ELISA procedure (a sandwich or double antibody ELISA), the Immunolon I microtiter plate was coated with 1 to 40,000 dilution of partially purified goat IgG and incubated for 2 hrs at 25° C., the wells were washed once with phosphate buffered saline (PBS) and open sites in the wells were blocked with 2% human serum in phosphate buffer. The wells were washed 3 times with PTB, 50 μl of the antigen sample (usually diluted 1:2 with PTB +0.15 M NaCL) was added to each well and incubated at 25° C. for 2 hrs, the wells were washed again with PTB, 50 μl of 1 to 200 dilution of IgM in PBT was added and incubated at 25° C. for 2 hrs, and the amount of IgM was measured as described above.

Both of these assays were used to measure purified antigen, purified antigen added to normal human serum, serum from cancer patients, extracts of tumors and other biological samples. The first assay worked better for more purified samples, the second assay worked better for samples like serum and other samples that contain a large number of other proteins that competed with the antigen for binding to the surface of the well because the antigen was absorbed out of the biological sample onto the goat antibody, and the monoclonal antibody was used to quantitate the amount of antigen. Both ELISA procedures were able to detect 10 ng of purified antigen.

The ELISA method is one of a variety of immunoassay techniques that could be employed to assay for cancer procoagulant antigen in biological samples. Other methods include radioimmunoassay, immunoinhibition assay, immunofluorescent assay and immunoprecipitation assay; all such assays that include the use of an antibody to quantitate the cancer procoagulant antigen should be construed to be included under the description of the assay.

To prove the effectiveness of the ELISA according to the present invention to diagnose cancer, a large number of serum samples from documented cancer patients and non-cancer controls were tested in blind runs. Table 1 contains the data obtained from the immunoassays conducted and includes the categories of cancers evaluated, the number of individuals studied, the number of samples correctly identified, and the percentage of correctly identified samples.

TABLE I

| Tumor Type or Site | Total No. | Correct No. | % Correct |
| --- | --- | --- | --- |
| Gastrointestinal | 33 | 31 | 94 |
| Respiratory | 29 | 24 | 83 |
| Breast | 35 | 26 | 74 |
| Prostate | 6 | 6 | 100 |
| Bone | 4 | 4 | 100 |
| Lymphoma | 6 | 5 | 83 |
| Pancreatic | 8 | 7 | 88 |
| Other | 12 | 9 | 75 |
| Control Samples: | | | |
| Normal Controls | 107 | 98 | 92 |
| Benign Disease | 10 | 10 | 100 |
| Controls | | | |

From the foregoing description, one skilled in the art can easily ascertain the essential characteristics of my invention and without departing from the spirit and scope thereof, can make various changes and/or modifications to the invention for adapting it to various usages and conditions. Accordingly, such changes and modifications are properly intended to be within the full range of equivalents of the following claims.

Having thus described my invention and the manner and process of making and using it in such full, clear, concise, and exact terms as to enable any person skilled in the art to which it pertains, or with which it is most closely connected, to make and use the same, and having set forth the best modes for carrying out my invention;

I claim:

1. Monoclonal antibody to cancer procoagulant.
2. A method for producing monoclonal antibody to cancer procoagulant comprising the steps of:
   (a) immunizing an animal with cancer procoagulant antigen;
   (b) fusing spleen cells from said immunized animal with myeloma cells to form hybrid cells;
   (c) culturing said hybrid cells in a selective medium;
   (d) testing for the presence of the desired antibody;
   (e) cloning cells producing the desired antibody;
   (f) subjecting medium from said cells producing the desired antibody to the step of dissociating said antibody from cancer procoagulant antigen produced by the hybrid cells used for the production of said antibody; and
   (g) isolating the desired antibody.
3. The method of claim 2 wherein the step of dissociating comprises exposure to a dissociating condition selected from the group consisting of a dissociating agent, a pH adjustment and combinations of dissociating agents and pH adjustments.
4. The method of claim 3 wherein said dissociating agent is selected from the group consisting of at least about 3M urea and at least about 5M guanidine.
5. The method of claim 3 wherein said pH adjustment is selected from the group consisting of pH between about 2.0 and about 3.5 and pH between about 10.5 and about 12.0.
6. The method of claim 2 wherein the step of isolating the desired antibody comprises chromatographic separation.
7. A reagent for detection of cancer procoagulant comprising monoclonal antibodies produced by the method of claim 36.
8. A method to diagnose cancer in a patient comprising assaying a biological sample of said patient for the presence of cancer procoagulant using monoclonal antibodies to cancer procoagulant and detecting the results of said assay.
9. A method of detecting cancer procoagulant in a biological sample of a cancer patient comprising contacting said biological sample with a reagent which contains monoclonal antibodies to cancer procoagulant and detecting the presence or absence of an immunological reaction.

* * * * *